United States Patent [19]

Wepplo

[11] Patent Number: 4,460,776

[45] Date of Patent: Jul. 17, 1984

[54] PROCESS FOR THE PREPARATION OF 6-SUBSTITUTED-2,3-PYRIDINEDICARBOXYLIC ACID DIESTERS

[75] Inventor: Peter J. Wepplo, Princeton, N.J.

[73] Assignee: American Cyanamid Company, Stamford, Conn.

[21] Appl. No.: 381,826

[22] Filed: May 25, 1982

[51] Int. Cl.³ .......................................... C07D 213/813
[52] U.S. Cl. ................................................... 546/250
[58] Field of Search ........................................ 546/250

[56] References Cited

FOREIGN PATENT DOCUMENTS 1207930 12/1965 Fed. Rep. of Germany ...... 546/250

Primary Examiner—Henry R. Jiles
Assistant Examiner—Bernard Dentz
Attorney, Agent, or Firm—H. G. Jackson

[57] ABSTRACT

There is provided a process for the preparation of 6-substituted-2,3-pyridinedicarboxylic acid diesters useful as intermediates in the manufacture of herbicidally active 2-(2-imidazolin-2-yl)pyridine compounds.

6 Claims, No Drawings

PROCESS FOR THE PREPARATION OF 6-SUBSTITUTED-2,3-PYRIDINEDICARBOXYLIC ACID DIESTERS

SUMMARY OF THE INVENTION

The invention relates to a process for the preparation of 6-substituted-2,3-pyridinedicarboxylic acid diesters which are useful as intermediates in the manufacture of the herbicidally effective 2-(2-imidazolin-2-yl)pyridine compounds described in the application for United States Letters Patent of Marinus Los, Ser. No. 382,041, filed concurrently herewith and incorporated herein by reference.

The process of the invention involves reaction of a formula (I) acetylenic ketone, having the structure: Z—CO—C≡CH, wherein Z is hydrogen, $C_1$–$C_6$ alkyl or phenyl optionally substituted with $C_1$–$C_4$ alkyl, halogen (including fluorine, chlorine, bromine and iodine but preferably chlorine), $C_1$–$C_4$ alkoxy, nitro or $C_1$–$C_4$ alkylthio; with a formula II aminomaleate having the structure:

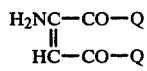

wherein Q is $C_1$–$C_4$ alkoxy; or an aminofumarate, shown as formula III, having the structure:

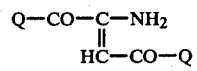

wherein Q is $C_1$–$C_4$ alkoxy. In this reaction, the ratio of acetylenic ketone to aminomaleate or aminofumarate is preferably about 1:1 and the reaction is generally carried out in the presence of a polar solvent such as dimethylformamide (DMF), acetonitrile or a $C_1$–$C_4$ alcohol, preferably methanol, at a temperature between 50° C. and 100° C. This reaction yields the 6-substituted-2,3-pyridinedicarboxylic acid diester of formula IV. The reaction may be graphically illustrated as follows:

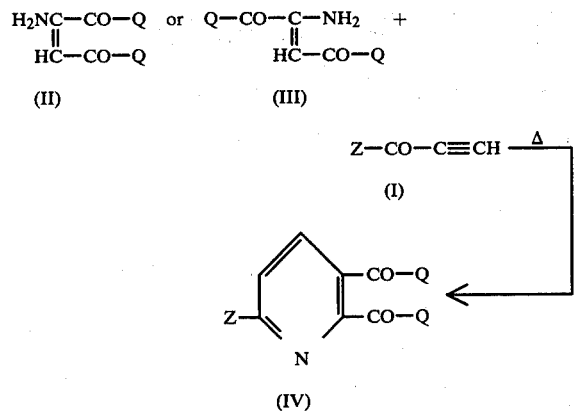

wherein Q and Z are as described above.

The formula (IV) diester may then be hydrolyzed to the corresponding 6-substituted-2,3-pyridinedicarboxylic acid, shown as formula (V), by reaction thereof with a strong base such as potassium hydroxide or sodium hydroxide, at a temperature between 35° and 100°. This reaction is generally carried out in the presence of a $C_1$–$C_4$ alcohol, preferably methanol or ethanol. Thereafter, the reaction mixture is treated with a strong mineral acid, such as sulfuric acid, ice and a $C_1$–$C_4$ alcohol preferably methanol. The mixture is cooled, diluted with a ketonic solvent such as acetone, then treated with solid sodium sulfate and filtered. The filtrate is concentrated, the residue triturated with ether and the diacid removed by filtration. Treatment of the formula (V) 6-substituted-2,3-pyridinedicarboxylic acid with, for example, acetic anhydride in the presence of dimethoxyethane (DME) and pyridine yields the formula (VI) 6-substituted-2,3-pyridinedicarboxylic acid anhydride. These reactions may be graphically illustrated as follows:

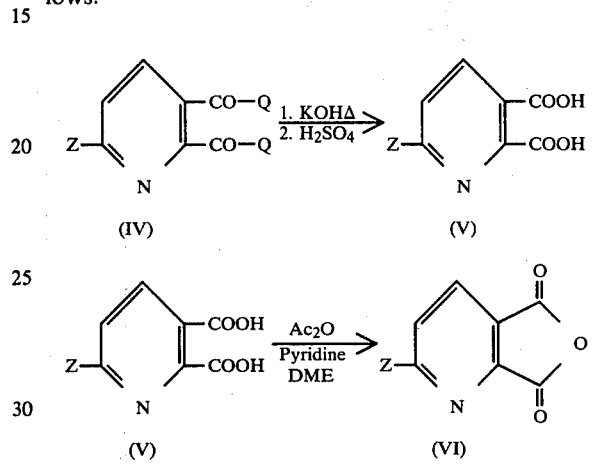

wherein Q is $C_1$–$C_4$ alkoxy and Z is hydrogen, $C_1$–$C_6$ alkyl, or phenyl optionally substituted with $C_1$–$C_4$ alkyl, halogen, $C_1$–$C_4$ alkoxy, nitro or $C_1$–$C_4$ alkylthio.

Reaction of the formula (VI) 6-substituted-pyridine-2,3-dicarboxylic acid anhydride with an aminocarboxamide depicted as formula (VII) or an aminothiocarboxamide depicted by formula (VIII), preferably in the presence of an organic solvent such as tetrahydrofuran, under a blanket of inert gas such as nitrogen or argon, yields a mixture of the isomeric pyridine monoacid-monoamide products represented by formulas (IX) and (X).

The solvent is then removed in vacuo and the oily product containing the isomeric pyridine monoacid-monoamide products dissolved in strong base, such as 6N sodium hydroxide. The thus-formed mixture is then heated to a temperature between about 50° and 100° C. and preferably between 60° and 80° C., under a blanket of inert gas such as nitrogen. The mixture is cooled and the pH thereof adjusted to between pH 8 and 10 and preferably to pH 8.5 to 9.5, with a strong mineral acid such as sulfuric acid. The reaction mixture is extracted with an organic solvent such as ether and the organic extracts discarded. The aqueous phase is then adjusted to a pH between about 2 and 4 and preferably about pH 3 with a strong mineral acid such as sulfuric acid. The resulting precipitate is removed by any convenient means, such as filtration, washed with water and dried to give the herbicidally effective formula (XI) 6-substituted-2-(2-imidazolin-2-yl)nicotinic acid.

By the same procedure, but substituting the appropriate aminothiocarboxamide for the formula (VII) aminocarboxamide, one obtains the herbicidally effective thiono derivative of the 6-substituted-2-(2-imidazolin-2-yl)nicotinic acid.

The above-described base-catalyzed cyclization of the formula (IX) and (X) 6-substituted-2,3-pyridinedicarboxylic acid monoamides is described in the application for United States Letters Patent of Jerry Michael Barton, Don Wesley Long and Kenneth Dale Lotts, Ser. No. 381,818, filed concurrently herewith and incorporated herein by reference and now abandoned.

This base-catalyzed cyclization is graphically illustrated below:

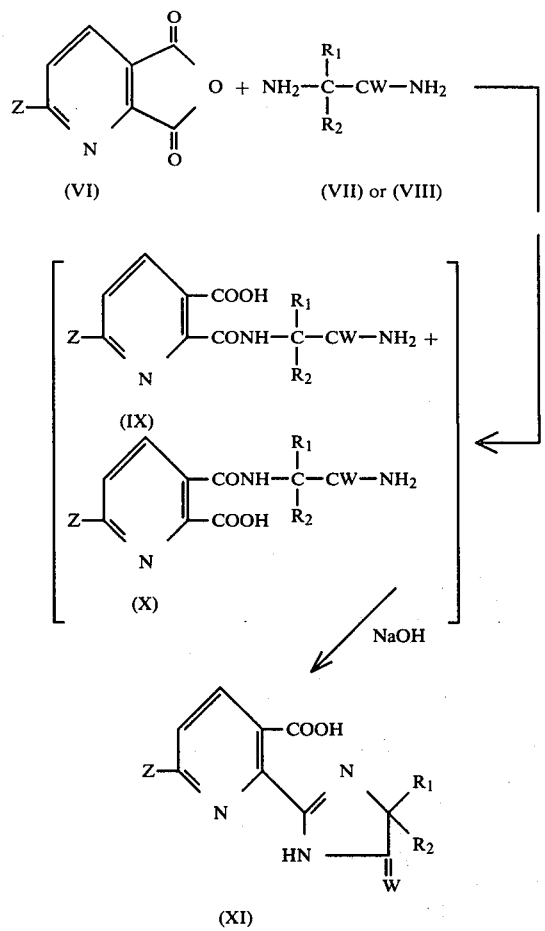

wherein Z is hydrogen, $C_1$-$C_6$ alkyl or phenyl optionally substituted with $C_1$-$C_4$ alkyl, halogen, $C_1$-$C_4$ alkoxy, nitro or $C_1$-$C_4$ alkylthio; W is sulfur or oxygen; $R_1$ is $C_1$-$C_4$ alkyl; $R_2$ is $C_1$-$C_4$ alkyl or $C_3$-$C_6$ cycloalkyl; and when $R_1$ and $R_2$ are taken together they may represent $C_3$-$C_6$ cycloalkyl optionally substituted with methyl and when $R_1$ and $R_2$ are not the same, the optical isomers thereof.

The formula (XI) 6-substituted-2-(2-imidazolin-2-yl)nicotinic acids are effective herbicidal agents useful for the control of a wide variety of herbaceous and woody annual and perennial monocotyledonous and dicotyledonous plants. Moreover, these compounds are herbicidally effective for controlling weeds indigenous to both dry land and wet land areas. They are also useful as aquatic herbicides and are unique in their effectiveness in controlling the above-said plants when applied to the foliage thereof or to soil or water containing seeds or other propagating organs of said plants such as tubers, rhizomes or stolons, at rates of from about 0.025 to 8.0 kg/ha.

The formula (XI) 6-substituted-2-(2-imidazolin-2-yl)nicotinic acids can be formulated as wettable powders, flowable concentrates, emulsifiable concentrates, granular formulations and the like for application to undesirable plant species for the control thereof.

Wettable powders can be prepared by grinding together about 20% to 45% by weight of a finely divided carrier such as kaolin, bentonite, diatomaceous earth, attapulgite, or the like, 45% to 80% by weight of the active compound, 2% to 5% by weight of a dispersing agent such as sodium lignosulfonate, and 2% to 5% by weight of a nonionic surfactant, such as octylphenoxy polyethoxy ethanol, nonylphenoxy polyethoxy ethanol or the like.

A typical flowable liquid can be prepared by admixing about 40% by weight of the active ingredient with about 2% by weight of a gelling agent such as bentonite, 3% by weight of a dispersing agent such as sodium lignosulfonate, 1% by weight of polyethylene glycol and 54% by weight of water.

A typical emulsifiable concentrate can be prepared by dissolving about 5% to 25% by weight of the active ingredient in about 65% to 90% by weight of N-methylpyrrolidone, isophorone, butylcellosolve, methylacetate or the like and dispersing therein about 5% to 10% by weight of a nonionic surfactant such as alkylphenoxy polyethoxy alcohol. This concentrate is dispersed in water for application as a liquid spray.

When the compounds of the invention are to be used as herbicides where soil treatments are involved, the compound may be prepared and applied as granular products. Preparation of the granular product can be achieved by dissolving the active compound in a solvent such as methylene chloride, N-methylpyrrolidone or the like and spraying the thus prepared solution on a granular carrier such as corncob grits, sand, attapulgite, kaolin or the like.

The granular product thus prepared generally comprises about 3% to 20% by weight of the active ingredient and about 97% to 80% by weight of the granular carrier.

In order to facilitate a further understanding of the invention, the following examples are presented primarily for the purpose of illustrating certain more specific details thereof. The invention is not to be deemed limited thereby except as defined in the claims. Unless otherwise noted, all parts are by weight.

EXAMPLE 1

A. Preparation of 6-phenyl-2,3-pyridinedicarboxylic acid dimethyl ester

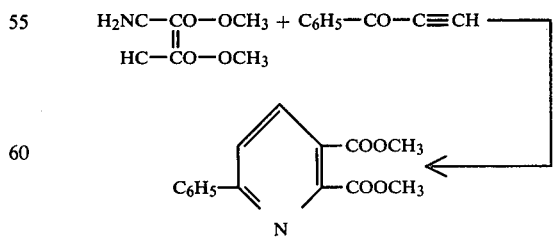

A suspension of 3.18 g (20 mmol) of dimethyl 2-aminomaleate and 2.6 g (20 mmol) of phenyl ethynyl ketone in 10 ml of methanol is heated at reflux overnight. The methanol is removed in vacuo, and the residue is digested in ether and filtered to give 2.52 g of the desired diester as a tan solid, mp 124.5°–127° C.

B. Preparation of 6-phenyl-2,3-pyridinedicarboxylic acid dimethyl ester

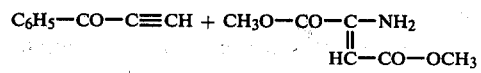

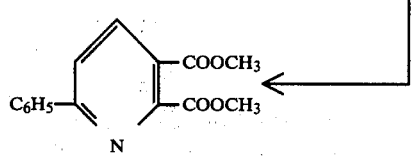

A solution of 11.66 g (73.5 mmol) of dimethyl 2-aminofumarate and 9.5 g (73 mmol) of phenyl ethynyl ketone in 35 ml of methanol is heated at reflux overnight. The reaction is allowed to cool to room temperature, and 10 g of crude diester is collected by filtration. The crude diester is dissolved in dichloromethane-methanol mixture and treated with charcoal, filtered, concentrated and the residue crystallized to give 9.1 g of the desired diester as a white solid, mp 124°–127° C.

The above experiments show that when either the aminofumarate or aminomaleate is used in this reaction, the same product is produced.

Using essentially the same procedure as described above, but substituting the appropriate ethynyl ketone for phenyl ethynyl ketone and using either the maleate, fumarate or mixture of these, the following pyridine-2,3-dimethyl esters are prepared.

| Z | mp °C. or bp °C./pressure |
|---|---|
| Cl—C$_6$H$_4$— | 119.5–122° |
| CH$_3$—C$_6$H$_4$— | 106.0–107.5° |
| C$_2$H$_5$ | 122.0–127°/0.25 mm |
| n-C$_3$H$_7$ | 151.0–155°/0.3 mm |
| i-C$_3$H$_7$ | 131.0–135°/0.15 mm |
| CH$_3$ | 67–70° |

EXAMPLE 2

Preparation of 6-propyl-2,3-pyridinedicarboxylic acid

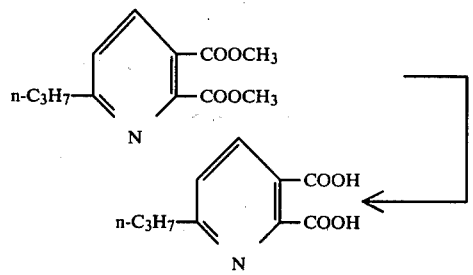

To a stirred solution under nitrogen containing 17.25 g of diester in 75 ml dry methanol is added 19.2 g potassium hydroxide with cooling to control the exotherm. The mixture is heated under reflux for one and one-half hours. Then a mixture of 10.4 ml concentrated H$_2$SO$_4$, 19.1 g ice, and 25 ml methanol is added. The mixture is cooled, diluted with 350 ml acetone, and solid sodium sulfate added. The mixture is filtered, and the filtrate concentrated. The residue is triturated with ether. The crystalline diacid is removed by filtration. A sample is recrystallized from acetone-hexane to give analytically pure 6-propyl-2,3-pyridinedicarboxylic acid, mp 149°–153° C.

The following acids are prepared similarly by substituting the appropriate substituted pyridine diester for dimethyl 6-propyl-2,3-pyridinedicarboxylate.

| Y | Z | mp °C. |
|---|---|---|
| H | i-C$_3$H$_7$ | 121.5–124° |
| H | CH$_3$—C$_6$H$_4$— | 243.0–253° |
| H | Cl—C$_6$H$_4$— | >245.0° |
| H | C$_2$H$_5$ | 155.5–157° |
| H | C$_6$H$_5$— | 162.0–164° |
| H | CH$_3$ | 164° |

EXAMPLE 3

Preparation of 6-phenyl-2,3-pyridinedicarboxylic acid anhydride

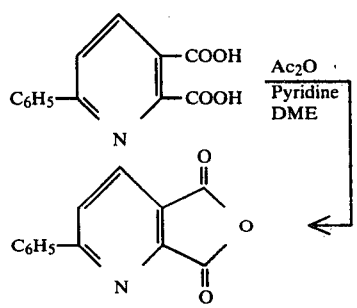

To a solution of 5.56 g (22.9 mmol) of 6-phenyl-2,3-pyridinedicarboxylic acid and 7 ml (121.8 mmol) of acetic anhydride in 25 ml of dimethoxyethane (DME) is added 3.7 ml (45.7 mmol) of pyridine. A small exotherm ensues, and the anhydride begins to precipitate. After one hour, the reaction mixture is diluted with ether and hexane to the cloud point, chilled in an ice bath, and filtered. The solid is washed with ether to give 4.73 g of the desired anhydride as a white solid, mp 187°–192° C.

Using essentially the same procedure as described above but substituting the appropriate 2,3-pyridinedicarboxylic acid for 6-phenyl-2,3-pyridinedicarboxylic acid, the following anhydrides are prepared. Many of these are used without fall characterization since they are sensitive to atmospheric moisture.

| X | Y | Z | mp °C. |
|---|---|---|---|
| H | H | Cl—⟨⟩— | Solid |
| H | H | CH$_3$—⟨⟩— | Solid |
| H | H | C$_2$H$_5$ | 65–67° |
| H | H | C$_3$H$_7$ | Oil |
| H | H | i-C$_3$H$_7$ | Oil |
| H | H | CH$_3$ | 106–108.5° |

EXAMPLE 4

Preparation of 2-amino-2,3-dimethylbutyramide

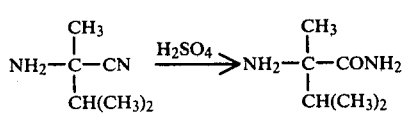

To concentrated sulfuric acid (29.7 ml), cooled with stirring in an ice-acetone cooling bath, is added 11.8 g (−)-2-amino-2,3-dimethylbutyronitrile with $[\alpha]_D^{25} = 7.31°$ (c=0.0368 g/ml THF) at such a rate that the temperature does not go above 25° C. After the addition, the temperature of the reaction mixture is slowly raised to 100° C. and held at that temperature for one hour. After cooling the mixture in an ice-acetone bath, 85 ml concentrated ammonium hydroxide is added at such a rate that the temperature does not exceed 75° C. The mixture is extracted five times with methylene chloride, the combined extracts dried and concentrated. This gives 11.95 g of white solid, mp 79°–81° C. and $[\alpha]_D^{25} = +57.43°$ (c=0.0213 g/ml THF). This solid is recrystallized from methylene chloride-hexane to give 11.2 g of (+)-2-amino-2,3-dimethylbutyramide, mp 81°–82° C. $[\alpha]_D^{25} = +59.38°$ (c=0.0162 g/ml THF).

In a similar way, hydrolysis of the (+)-2-amino-2,3-dimethylbutyronitrile with sulfuric acid yields the (−)-2-amino-2,3-dimethylbutyramide, mp 81°–82° C., $[\alpha]_D^{25} = -57.14°$ (c=0.0654 g/ml THF).

In a similar way, hydrolysis of the (±)-2-amino-2,3-dimethylbutyronitrile with sulfuric acid yields (±)-2-amino-2,3-dimethylbutyramide, mp 74.5°–76° C.

EXAMPLE 5

Preparation of 2-amino-2,3-dimethylthiobutyramide

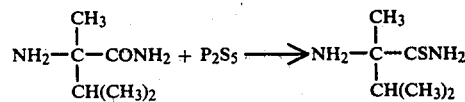

A stirred mixture containing 39 g of 2-amino-2,3-dimethylbutyramide and 73.3 g phosphorus penta-sulfide in 1 L dry dioxane is heated at reflux for four hours. After stirring at room temperature for 72 hours, the mixture is again heated at reflux for two hours, the mixture is cooled, concentrated, and the residue distributed between water and methylene chloride. The aqueous phase is separated, the pH adjusted to 8 with concentrated ammonium hydroxide and extracted three times with methylene chloride. All the organic phases were combined, dried and concentrated to give 22.47 g product, mp 78°–85° C. Recrystallization of this material first from ethyl acetate and then methylene chloride-pentane gives analytically pure 2-amino-2,3-dimethylthiobutyramide with mp 98°–100° C.

EXAMPLE 6

Preparation of 6-isopropyl-2-(5-isopropyl-5-methyl-4-oxo-2-imidazolin-2-yl)nicotinic acid

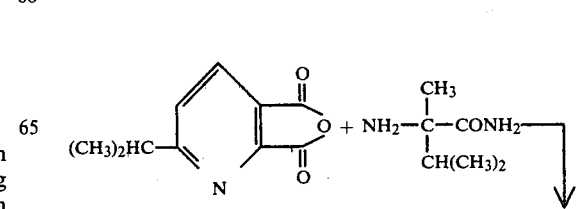

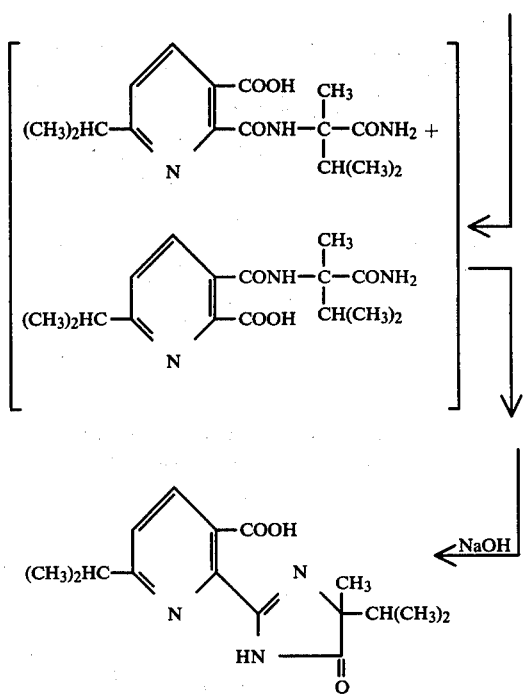

To a stirred solution of the anhydride (15.1 g) in 125 ml THF under nitrogen is added 11.4 of 2-amino-2,3-dimethylbutyramide. The mixture is stirred overnight. The solvent is removed in vacuo, and the resulting oil (consisting of a mixture of the isomeric pyridine monoacid-monoamide products) dissolved in 66 ml of 6N NaOH. This solution is heated at 70° C. under nitrogen for three and one-half hours, then cooled and the pH of the solution adjusted to 9 with 6N $H_2SO_4$. The mixture is extracted twice with ether, and the organic extracts discarded. The pH of the aqueous phase is adjusted to 3 with 6N $H_2SO_4$. The resulting precipitate is removed by filtration, washed with water and dried to give 13.25 g of desired product. A sample is recrystallized from methylene chloride-hexane followed by ether-hexane to give an analytically pure sample of 6-isopropyl-2-(5-isopropyl-5-methyl-4-oxo-2-imidazolin-2-yl)nicotinic acid, mp 131°–133.5° C.

By using essentially the same procedure but substituting the appropriate substituted 2,3-pyridinedicarboxylic acid anhydride for 6-isopropyl-2,3-pyridinedicarboxylic acid anhydride and also substituting, if necessary, the optically active 2-amino-2,3-dimethylbutyramide or the 2-amino-2,3-dimethylthiobutyramide for 2-amino-2,3-dimethylbutyramide, the following nicotinic acids were prepared.

| X | Y | Z | mp °C. |
|---|---|---|---|
| H | H | $CH_3$ | 145.0–146.5 |
| H | H | H | 128.0–131.0 $[\alpha]_D^{25} = +18.37$ (C = 0.0902 g/ml THF) |
| H | H | $C_3H_7$ | 148.5–150.5 |
| H | H | Cl—⌬— | 247.0–249.0 |
| H | H | $CH_3$—⌬— | 215.5–218.5 |
| H | H | ⌬— | 252.0–254.0 |
| H | H | $C_2H_5$ | 118.0–122.0 |
| H | H | H | 170.0–172.5 | mp 182–184

EXAMPLE 7

Post-emergence herbicidal evaluation of test compounds

The post-emergence herbicidal activity of the compounds of the present invention is demonstrated by the following tests, wherein a variety of monocotyledonous and dicotyledonous plants are treated with test compounds dispersed in aqueous acetone mixtures. In the tests, seedling plants are grown in jiffy flats for about two weeks. The test compounds are dispersed in 50/50 acetone/water mixtures containing 0.5% TWEEN ®20, a polyoxyethylene sorbitan monolaurate surfactant of Atlas Chemical Industries, in sufficient quantity to provide the equivalent of about 0.025 kg to 8 kg per hectare of active compound when applied to the plants through a spray nozzle operating at 40 psi for a predetermined time. After spraying, the plants are placed on greenhouse benches and are cared for in the usual manner, commensurate with conventional greenhouse practices. From 4 to 5 weeks after treatment, the seedling plants, are examined and rated according to the rating system provided below. The data obtained are recorded in Table I below.

| Rating System | % Difference in Growth from the Check* |
|---|---|
| 0 No effect | 0 |
| 1 Possible effect | 1–10 |
| 2 Slight effect | 11–25 |
| 3 Moderate effect | 26–40 |
| 5 Definite injury | 41–60 |
| 6 Herbicidal effect | 61–75 |
| 7 Good Herbicidal effect | 76–90 |
| 8 Approaching complete kill | 91–99 |
| 9 Complete kill | 100 |
| 4 Abnormal growth, that is, a definite physiological malformation but with an over-all effect less than a 5 on the rating scale. | |

In most cases the data are for a single test, but in several instances, they are average values obtained from more than one test.

| Plant Species Used | |
|---|---|
| Barnyardgrass | (Echinochloa crusgalli) |
| Green foxtail | (Setaria viridis) |
| Purple Nutsedge | (Cyperus rotundus L.) |
| Wild Oats | (Avena Fatua) |
| Quackgrass | (Agropyron repens) |
| Field Bindweed | (Convolvulus arvensis L.) |
| Morningglory | (Ipomoea purpurea) |
| Ragweed | (Ambrosia artemisiifolia) |
| Velvetleaf | (Abutilon Theophrasti) |
| Barley | (Hordeum vulgare) |
| Corn | (Zea mays) |
| Rice | (Oryza Sativa) |
| Soybean | (Glycine max) |
| Sunflower | (Helianthus annus) |
| Wheat | (Triticum aestivum) |

TABLE I

POST-EMERGENCE TESTS - RATES IN KG/HA

| Compound | RATE | BARNY ARDGR | GREEN FOX | P NUT SEDGE | WILD OATS | QUACK GRASS | FLD B INDWD | MRNGL RY SP | RAGWE ED | VELVE TLEAF | S BAR LY LA | CORN FIELD | RICE, NATO | SOYBE AN WI | SUNFL R XXX | S WHE AT ER |
|---|---|---|---|---|---|---|---|---|---|---|---|---|---|---|---|---|
| 2-(5-Isopropyl-5-methyl-4-oxo-2-imidazolin-2-yl)-nicotinic acid | 10.000 | 9.0 | 9.0 | 9.0 | 9.0 | | | 7.0 | 9.0 | 9.0 | | | | | 9.0 | 9.0 |
| | 2.000 | 9.0 | 9.0 | 9.0 | 9.0 | | 8.8 | 8.0 | 8.0 | 9.0 | | | 9.0 | 9.0 | 9.0 | 9.0 |
| | 1.000 | 9.0 | 9.0 | 9.0 | 9.0 | 9.0 | 9.0 | 8.8 | 8.6 | 9.0 | 9.0 | 9.0 | 9.0 | 9.0 | 9.0 | 9.0 |
| | .500 | 8.9 | 9.0 | 8.7 | 9.0 | 9.0 | 8.9 | 8.8 | 8.6 | 8.9 | 9.0 | 9.0 | 8.8 | 9.0 | 9.0 | 9.0 |
| | .250 | 9.0 | 9.0 | 8.8 | 9.0 | 8.9 | 8.9 | 8.9 | 7.4 | 8.9 | 9.0 | 9.0 | 8.7 | 8.7 | 9.0 | 9.0 |
| | .125 | 9.0 | 9.0 | 8.4 | 9.0 | 9.0 | 9.0 | 9.0 | 9.0 | 9.0 | 9.0 | 9.0 | 9.0 | | 9.0 | 9.0 |
| (+)-2-(5-Isopropyl-5-methyl-4-oxo-2-imidazolin-2-yl)-nicotinic acid | 1.000 | 9.0 | 9.0 | 9.0 | 9.0 | 9.0 | 9.0 | 9.0 | 9.0 | 9.0 | 9.0 | 9.0 | 9.0 | | 9.0 | 9.0 |
| | .500 | 9.0 | 9.0 | 9.0 | 9.0 | 9.0 | 9.0 | 9.0 | 9.0 | 9.0 | 9.0 | 9.0 | 9.0 | | 9.0 | 9.0 |
| | .250 | 9.0 | 9.0 | 9.0 | 9.0 | 9.0 | 9.0 | 9.0 | 9.0 | 9.0 | 9.0 | 9.0 | 9.0 | | 9.0 | 9.0 |
| | .125 | 9.0 | 9.0 | 9.0 | 9.0 | 9.0 | 9.0 | 9.0 | 9.0 | 9.0 | 9.0 | 9.0 | 9.0 | | 9.0 | 9.0 |
| 2-(5-Isopropyl-5-methyl-4-oxo-2-imidazolin-2-yl)-6-phenyl-nicotinic acid | 4.000 | 9.0 | 9.0 | 7.0 | 9.0 | 9.0 | 9.0 | 6.0 | 6.0 | 7.0 | | 9.0 | 8.0 | | 9.0 | 4.0 |
| | 1.000 | 9.0 | 9.0 | 3.0 | 7.0 | 2.0 | 6.0 | 4.0 | 4.0 | 2.0 | | 9.0 | 4.0 | | 9.0 | 2.0 |
| | .500 | 8.0 | 9.0 | 3.0 | 3.0 | | 8.0 | 3.0 | 1.0 | 2.0 | | 6.0 | | | 9.0 | 2.0 |
| | .250 | 8.0 | 7.0 | 2.0 | 2.0 | 2.0 | 5.0 | 1.0 | 0.0 | 0.0 | | 6.0 | 3.0 | | 9.0 | 1.0 |
| 2-(5-Isopropyl-5-methyl-4-oxo-2-imidazolin-2-yl)-6-methyl-nicotinic acid | 4.000 | 9.0 | 9.0 | 9.0 | 9.0 | 9.0 | 9.0 | 9.0 | 9.0 | 9.0 | | 9.0 | 9.0 | | 9.0 | 9.0 |
| | 1.000 | 9.0 | 9.0 | 9.0 | 9.0 | 9.0 | 9.0 | 9.0 | 8.5 | 9.0 | | 9.0 | 9.0 | | 9.0 | 9.0 |
| | .500 | 9.0 | 9.0 | 9.0 | 9.0 | 9.0 | 9.0 | 9.0 | 7.0 | 9.0 | | 9.0 | 8.0 | | 9.0 | 9.0 |
| | .250 | 9.0 | | 8.0 | 9.0 | 9.0 | | 9.0 | 5.0 | 9.0 | | 9.0 | 7.0 | | 9.0 | 9.0 |
| | .125 | 9.0 | | 9.0 | 9.0 | 9.0 | 9.0 | 9.0 | 9.0 | 9.0 | | 9.0 | 9.0 | | 9.0 | 9.0 |
| 2-(5-Isopropyl-5-methyl-4-thiono-2-imidazolin-2-yl)nicotinic acid | 1.000 | 9.0 | | 9.0 | 9.0 | 9.0 | 9.0 | 9.0 | 9.0 | 9.0 | | 9.0 | 9.0 | | 9.0 | 9.0 |
| | .500 | 9.0 | | 9.0 | 9.0 | 9.0 | 9.0 | 9.0 | 9.0 | 9.0 | | 9.0 | 9.0 | | 9.0 | 9.0 |
| | .250 | 8.0 | | 8.0 | 9.0 | 9.0 | 9.0 | 9.0 | 7.0 | 8.0 | | 9.0 | 8.0 | | 9.0 | 6.0 |
| 6-Ethyl-2-(5-isopropyl-5-methyl-4-oxo-2-imidazolin-2-yl)nicotinic acid | .250 | 8.0 | | 9.0 | 8.0 | 9.0 | 9.0 | 9.0 | 5.0 | 8.0 | | 9.0 | 8.0 | | 9.0 | 6.0 |
| | .125 | 8.0 | | 7.0 | 5.0 | 8.0 | 9.0 | 8.0 | 3.0 | 3.0 | | 9.0 | 7.0 | | 9.0 | 4.0 |
| 2-(5-Isopropyl-5-methyl-4-oxo-2-imidazolin-2-yl)-6-propylnicotinic acid | 1.000 | 9.0 | | 8.0 | 9.0 | 9.0 | 8.0 | 9.0 | 9.0 | 9.0 | | 9.0 | 9.0 | | 9.0 | 9.0 |
| | .500 | 8.0 | | 7.0 | 8.0 | 9.0 | 9.0 | 9.0 | 8.0 | 9.0 | | 9.0 | 9.0 | | 9.0 | 9.0 |
| | .250 | 8.0 | | 7.0 | 7.0 | 9.0 | 9.0 | 8.0 | 3.0 | 3.0 | | 9.0 | 8.0 | | 9.0 | 8.0 |
| | .125 | 8.0 | | 4.0 | 3.0 | 7.0 | 6.0 | 5.0 | 1.0 | 3.0 | | 9.0 | 6.0 | | 9.0 | 6.0 |
| 6-butoxy-2-(5-isopropyl-5-methyl-4-oxo-2-imidazolin-2-yl) nicotinic acid | 8.0 | 9.0 | 9.0 | 9.0 | 9.0 | 9.0 | 9.0 | 9.0 | 7.0 | 7.0 | | | | | | |
| 2-(5-Isopropyl-5-methyl-4-oxo-2-imidazolin-2-yl)-6-p-tolyl-nicotinic acid | 1.000 | 0.0 | | 0.0 | 7.0 | 0.0 | 0.0 | 0.0 | 0.0 | 0.0 | 8.0 | 6.0 | 3.0 | 5.0 | 2.0 | |
| | .500 | 0.0 | | 0.0 | 7.0 | 0.0 | 0.0 | 0.0 | 0.0 | 0.0 | 8.0 | 6.0 | 2.0 | 5.0 | 0.0 | |
| | .250 | 0.0 | | 0.0 | 0.0 | 0.0 | 0.0 | 0.0 | 0.0 | 0.0 | 7.0 | 4.0 | 0.0 | 4.0 | 0.0 | |
| | .125 | 0.0 | | 0.0 | 0.0 | 0.0 | 0.0 | 0.0 | 0.0 | 0.0 | 7.0 | 3.0 | 0.0 | 3.0 | 0.0 | |
| | .063 | 0.0 | | 0.0 | 0.0 | 0.0 | 0.0 | 0.0 | 0.0 | 0.0 | 3.0 | 2.0 | 0.0 | 1.0 | 0.0 | |
| | .032 | 0.0 | | 0.0 | 0.0 | 0.0 | 0.0 | 0.0 | 0.0 | 0.0 | 2.0 | 1.0 | 0.0 | 0.0 | 0.0 | |

EXAMPLE 8

Pre-emergence herbicidal evaluation of test compounds

The pre-emergence herbicidal activity of the compounds prepared by the process of the invention is exemplified by the following tests in which the seeds of a variety of monocotyledonous and dicotyledonous plants are separately mixed with potting soil and planted on top of approximately one inch of soil in separate pint cups. After planting, the cups are sprayed with the selected aqueous acetone solution containing test compound in sufficient quantity to provide the equivalent of about 0.025 to 8 kg per hectare of test compound per cup. The treated cups are then placed on greenhouse benches, watered and cared for in accordance with conventional greenhouse procedures. From 4 to 5 weeks after treatment, the tests are terminated and each cup is examined and rated according to the rating system set forth above. The herbicidal proficiency of the active ingredients is evident from the test results which are recorded in Table II below. Where more than one test is involved for a given compound, the data are averaged.

TABLE II

PRE-EMERGENCE TESTS - RATES IN KG/HA

| Compound | RATE | BARNY ARDGR | GREEN FOX | P NUT SEDGE | WILD OATS | QUACK GRASS | FLD B INDWD | MRNGL RY SP | RAGWE ED | VELVE TLEAF | S BAR LY LA | CORN FIELD | RICE, NATO | SOYBE AN WI | SUNFL R XXX | S WHE AT ER |
|---|---|---|---|---|---|---|---|---|---|---|---|---|---|---|---|---|
| 2-(5-Isopropyl-5-methyl-4-oxo-2-imidazolin-2-yl)-nicotinic acid | 10.000 | 8.0 | 9.0 | 9.0 | 8.0 | | | 8.0 | 8.0 | 8.0 | 9.0 | 9.0 | 9.0 | 8.0 | 9.0 | 9.0 |
| | 2.000 | 9.0 | 9.0 | 9.0 | 9.0 | | | 8.0 | 9.0 | 9.0 | 9.0 | 9.0 | 9.0 | 8.5 | 9.0 | 9.0 |
| | 1.000 | 9.0 | 9.0 | 9.0 | 9.0 | 9.0 | 9.0 | 8.0 | 9.0 | 9.0 | 9.0 | 9.0 | 9.0 | 8.7 | 9.0 | 9.0 |
| | .500 | 9.0 | 9.0 | 9.0 | 9.0 | 9.0 | 9.0 | 8.7 | 8.8 | 8.8 | 9.0 | 9.0 | 9.0 | 8.7 | 9.0 | 9.0 |
| | .250 | 8.6 | 9.0 | 9.0 | 9.0 | 9.0 | 9.0 | 8.8 | 8.8 | 8.8 | 9.0 | 9.0 | 9.0 | 8.7 | 9.0 | 9.0 |
| | .125 | 9.0 | | 9.0 | 9.0 | 9.0 | 9.0 | 9.0 | 8.6 | 9.0 | 9.0 | 9.0 | 9.0 | | 9.0 | 9.0 |
| (+)-2-(5-Isopropyl-5-methyl-4-oxo-2-imidazolin-2-yl)-nicotinic acid | .500 | 9.0 | | 9.0 | 9.0 | 9.0 | 9.0 | 9.0 | 9.0 | 9.0 | 9.0 | 9.0 | 9.0 | | 9.0 | 9.0 |
| | .250 | 9.0 | | 9.0 | 9.0 | 9.0 | 9.0 | 9.0 | 9.0 | 9.0 | 9.0 | 9.0 | 9.0 | | 9.0 | 9.0 |
| | .125 | 9.0 | | 9.0 | 9.0 | 9.0 | 9.0 | 9.0 | 9.0 | 9.0 | 9.0 | 9.0 | 9.0 | | 9.0 | 9.0 |
| 2-(5-Isopropyl-5-methyl-4-oxo-2-imidazolin-2-yl)-6-phenyl-nicotinic acid | 4.000 | 3.0 | 4.0 | 9.0 | 3.0 | 9.0 | 9.0 | 4.0 | 4.0 | 7.0 | | 9.0 | 7.0 | | 9.0 | 5.0 |
| | 1.000 | 2.0 | 4.0 | 9.0 | 9.0 | 9.0 | 9.0 | 4.0 | 6.0 | 6.0 | | 9.0 | 5.0 | | 9.0 | 5.0 |
| | .500 | 2.0 | 4.0 | 9.0 | | 9.0 | 9.0 | | | 5.0 | | | | | 9.0 | 5.0 |
| 2-(5-Isopropyl-5-methyl-4-oxo-2-imidazolin-2-yl)-6-methyl-nicotinic acid | 4.000 | 9.0 | 9.0 | 9.0 | 9.0 | 9.0 | 9.0 | 9.0 | 9.0 | 9.0 | | 9.0 | 9.0 | | 9.0 | 9.0 |
| | 1.000 | 9.0 | 9.0 | 9.0 | 9.0 | 9.0 | 9.0 | 9.0 | 9.0 | 9.0 | | 9.0 | 9.0 | | 9.0 | 9.0 |
| | .500 | 9.0 | 9.0 | 9.0 | 9.0 | 9.0 | 9.0 | 9.0 | 9.0 | 9.0 | | 9.0 | 9.0 | | 9.0 | 9.0 |
| | .250 | 9.0 | 9.0 | 9.0 | 9.0 | 9.0 | 9.0 | 9.0 | 9.0 | 9.0 | | 9.0 | 9.0 | | 9.0 | 9.0 |
| 2-(5-Isopropyl-5-methyl-4-thiono-2-imidazolin-2-yl) nicotinic acid | .500 | 9.0 | 9.0 | 9.0 | 9.0 | 9.0 | 9.0 | 9.0 | 9.0 | 9.0 | | 9.0 | 9.0 | 9.0 | 9.0 | 9.0 |
| | .250 | 8.0 | 9.0 | 9.0 | 9.0 | 9.0 | 9.0 | 9.0 | 7.0 | 9.0 | | 9.0 | 9.0 | 9.0 | 9.0 | 9.0 |
| | .125 | 7.0 | 9.0 | 9.0 | 9.0 | 9.0 | 9.0 | 9.0 | 4.0 | 9.0 | | 9.0 | 9.0 | 8.0 | 9.0 | 9.0 |
| 6-Ethyl-2-(5-isopropyl-5-methyl-4-oxo-2-imidazolin-2-yl) nicotinic acid | .500 | 9.0 | | 9.0 | 8.0 | 9.0 | 9.0 | 9.0 | 9.0 | 9.0 | | 9.0 | 9.0 | | 9.0 | 9.0 |
| | .250 | 9.0 | | 9.0 | 7.0 | 9.0 | 9.0 | 9.0 | 9.0 | 8.0 | | 9.0 | 9.0 | | 9.0 | 7.0 |
| | .125 | 6.0 | | 9.0 | 7.0 | 9.0 | 9.0 | 9.0 | 9.0 | 7.0 | | 9.0 | 8.0 | | 8.0 | 7.0 |
| 2-(5-Isopropyl-5-methyl-4-oxo-2-imidazolin-2-yl)-6-propylnicotinic acid | .250 | 4.0 | | 8.0 | 5.0 | 8.0 | 9.0 | 7.0 | 6.0 | 7.0 | | 6.0 | 9.0 | 9.0 | 6.0 | 4.0 |
| | .125 | 4.0 | | 8.0 | 5.0 | 4.0 | 8.0 | 5.0 | | 4.0 | | 6.0 | 9.0 | 9.0 | 3.0 | 4.0 |
| 6-butoxy-2-(5-isopropyl-5-methyl-4-oxo-2-imidazolin-2-yl) nicotinic acid | 8.0 | 9.0 | 9.0 | 9.0 | 9.0 | 9.0 | 9.0 | 6.0 | 8.0 | 9.0 | | | | | | |
| 2-(5-Isopropyl-5-methyl-4-oxo-2-imidazolin-2-yl)-6-p-tolyl-nicotinic acid | .500 | 8.0 | | 6.0 | 4.0 | 9.0 | 4.0 | 8.0 | 0.0 | 6.0 | | 7.0 | 5.0 | 6.0 | 7.0 | 2.0 |
| | .250 | 2.0 | | 3.0 | 1.0 | 4.0 | 3.0 | 3.0 | 0.0 | 3.0 | | 2.0 | 3.0 | 5.0 | 6.0 | 1.0 |
| | .125 | 0.0 | | 1.0 | 0.0 | 2.0 | 1.0 | 1.0 | 0.0 | 2.0 | | 2.0 | 1.0 | 4.0 | 3.0 | 0.0 |

I claim:

1. A method for the preparation of compounds having the structure:

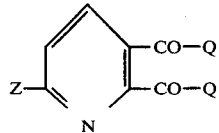

wherein Q is $C_1$-$C_4$ alkoxy and Z is hydrogen, $C_1$-$C_6$ alkyl or phenyl optionally substituted with $C_1$-$C_4$ alkyl, halogen, $C_1$-$C_4$ alkoxy, nitro or $C_1$-$C_4$ alkylthio; comprising reacting an acetylenic ketone having the structure: Z—CO—C≡CH, wherein Z is as described above, with an equivalent amount of an aminomaleate having the structure:

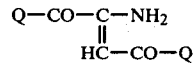

wherein Q is as described above, or an equivalent amount of an aminofumarate having the structure:

$$Q-CO-C-NH_2$$
$$\|$$
$$HC-CO-Q$$

wherein Q is as described above; in the presence of a polar solvent, optionally under a blanket of inert gas at a temperature between 50° C. and 100° C.

2. A method according to claim 1, wherein Z is $C_1$-$C_6$ alkyl and Q is methoxy.

3. A method according to claim 1, wherein the polar solvent is a $C_1$-$C_4$ alcohol, dimethylformamide or acetonitrile and the inert gas is nitrogen or argon.

4. A method according to claim 1, wherein Z is phenyl optionally substituted with fluorine, chlorine, bromine, iodine, or $C_1$-$C_6$ alkyl and Q is methoxy.

5. A method according to claim 1, wherein the polar solvent is methanol and the inert gas is nitrogen.

6. A method according to claim 1, wherein Z is hydrogen and Q is methoxy.

* * * * *